United States Patent [19]

Payne et al.

[11] Patent Number: 5,135,867
[45] Date of Patent: Aug. 4, 1992

[54] **GENE ENCODING A LEPIDOPTERAN-ACTIVE TOXIN FROM *BACILLUS THURINGIENSIS* ISOLATE DENOTED B.T. .PS81GG ACTIVE AGAINST LEPIDOPTERAN PESTS**

[75] Inventors: Jewel Payne; August J. Sick, both of San Diego; Mark Thompson, Del Mar, all of Calif.

[73] Assignee: Mycogen Corporation, San Diego, Calif.

[21] Appl. No.: 614,544

[22] Filed: Nov. 16, 1990

Related U.S. Application Data

[62] Division of Ser. No. 265,731, Nov. 1, 1988.

[51] Int. Cl.$^5$ .................. C12N 1/21; C12N 15/32; C12N 15/70
[52] U.S. Cl. .................. 435/252.33; 435/69.1; 435/252.3; 435/252.34; 435/320.1; 536/27

[58] Field of Search ................ 536/27; 435/69.1, 71.1, 435/91, 170, 172.1, 172.3, 252.1, 252.3, 252.34, 320.1, 252.33; 935/6, 9, 22, 59, 66, 72

[56] References Cited

U.S. PATENT DOCUMENTS 4,695,455 9/1987 Barnes et al. .................. 424/93

OTHER PUBLICATIONS

Adang et al., 1985, Gene, vol. 36:289–300.

Primary Examiner—Richard A. Schwartz
Assistant Examiner—Nancy T. Vogel
Attorney, Agent, or Firm—Saliwanchik & Saliwanchik

[57] ABSTRACT

A novel B.t. isolate with activity against lepidopteran insects is disclosed. This isolate is highly active against the beet armyworm. A gene from this isolate has been cloned. The DNA encoding the B.t. toxin can be used to transform various prokaryotic and eukaryotic microbes to express the B.t. toxin. These recombinant microbes can be used to control lepidopteran insects in various environments.

10 Claims, 25 Drawing Sheets

```
                    5                  10                 15
  1 Met Asp Asn Asn Pro Asn Ile Asn Glu Cys Ile Pro Tyr Asn Cys
 16 Leu Ser Asn Ala Pro Glu Val Glu Val Leu Gly Gly Glu Arg Ile Glu
 31 Thr Gly Tyr Thr Pro Ile Asp Ile Ser Leu Ser Leu Thr Gln Phe
 46 Leu Leu Ser Glu Phe Val Pro Gly Ala Gly Phe Val Leu Gly Leu
 61 Val Asp Ile Ile Trp Gly Ile Phe Gly Pro Ser Gln Trp Asp Ala
 76 Phe Leu Val Gln Ile Glu Gln Leu Ile Asn Gln Arg Ile Glu Glu
 91 Phe Ala Arg Asn Gln Ala Ile Ser Arg Leu Glu Gly Leu Ser Asn
106 Leu Tyr Gln Ile Tyr Ala Glu Ser Phe Arg Glu Trp Glu Ala Asp
121 Pro Thr Asn Pro Ala Leu Arg Glu Glu Met Arg Ile Gln Phe Asn
136 Asp Met Asn Ser Ala Leu Thr Thr Ala Ile Pro Leu Leu Ala Val
151 Gln Asn Tyr Gln Val Pro Leu Leu Ser Val Tyr Val Gln Ala Ala
166 Asn Leu His Leu Ser Val Leu Arg Asp Val Ser Val Phe Gly Gln
181 Arg Trp Gly Phe Asp Ala Ala Thr Ile Asn Ser Arg Tyr Asn Asp
196 Leu Thr Arg Leu Ile Gly Asn Tyr Thr Asp Tyr Ala Val Arg Trp
211 Tyr Asn Thr Gly Leu Glu Arg Val Trp Gly Pro Asp Ser Arg Asp
226 Trp Val Arg Tyr Asn Gln Phe Arg Arg Glu Leu Thr Leu Thr Val

241 Leu Asp Ile Val Ala Leu Phe Pro Asn Tyr Asp Ser Arg Arg Tyr
256 Pro Ile Arg Thr Val Ser Gln Leu Thr Arg Glu Ile Tyr Thr Asn
271 Pro Val Leu Glu Asn Phe Asp Gly Ser Phe Arg Gly Ser Ala Gln
286 Gly Ile Glu Arg Ser Ile Arg Ser Pro His Leu Met Asp Ile Leu
301 Asn Ser Ile Thr Ile Tyr Thr Asp Ala His Arg Gly Tyr Tyr Tyr
316 Trp Ser Gly His Gln Ile Met Ala Ser Pro Val Gly Phe Ser Gly
331 Pro Glu Phe Thr Phe Pro Leu Tyr Gly Thr Met Gly Asn Ala Ala
346 Pro Gln Gln Arg Ile Val Ala Gln Leu Gly Gln Gly Val Tyr Arg
361 Thr Leu Ser Ser Thr Phe Tyr Arg Arg Pro Phe Asn Ile Gly Ile
376 Asn Asn Gln Gln Leu Ser Val Leu Asp Gly Thr Glu Phe Ala Tyr
391 Gly Thr Ser Ser Asn Leu Pro Ser Ala Val Tyr Arg Lys Ser Gly
406 Thr Val Asp Ser Leu Asp Glu Ile Pro Pro Gln Asn Asn Asn Val
421 Pro Pro Arg Gln Gly Phe Ser His Arg Leu Ser His Val Ser Met
436 Phe Arg Ser Gly Ser Ser Ser Val Ser Ile Ile Arg Ala Pro
451 Met Phe Ser Trp Ile His Arg Ser Ala Glu Phe Asn Asn Ile Ile
466 Ala Ser Asp Ser Ile Thr Gln Ile Pro Ala Val Lys Gly Asn Phe

481 Leu Phe Asn Gly Ser Val Ile Ser Gly Pro Gly Phe Thr Gly Gly
496 Asp Leu Val Arg Leu Asn Ser Ser Gly Asn Asn Ile Gln Asn Arg
511 Gly Tyr Ile Glu Val Pro Ile His Phe Pro Ser Thr Ser Thr Arg
526 Tyr Arg Val Arg Val Arg Tyr Ala Ser Val Thr Pro Ile His Leu
541 Asn Val Asn Trp Gly Asn Ser Ser Ile Phe Ser Asn Thr Val Pro
556 Ala Thr Ala Thr Ser Leu Asp Asn Leu Gln Ser Ser Asp Phe Gly
571 Tyr Phe Glu Ser Ala Asn Ala Phe Thr Ser Ser Leu Gly Asn Ile
586 Val Gly Val Arg Asn Phe Ser Gly Thr Ala Gly Val Ile Ile Asp
601 Arg Phe Glu Phe Ile Pro Val Thr Ala Thr Leu Glu Ala Glu Tyr
616 Asn Leu Glu Arg Ala Gln Lys Ala Val Asn Ala Leu Phe Thr Ser
631 Thr Asn Gln Leu Gly Leu Lys Thr Asn Val Thr Asp Tyr His Ile
646 Asp Gln Val Ser Asn Leu Val Thr Tyr Leu Ser Asp Glu Phe Cys
661 Leu Asp Glu Lys Arg Glu Leu Ser Glu Lys Val Lys His Ala Lys
676 Arg Leu Ser Asp Glu Arg Asn Leu Leu Gln Asp Ser Asn Phe Lys
691 Asp Ile Asn Arg Gln Pro Glu Arg Gly Trp Gly Gly Ser Thr Gly
706 Ile Thr Ile Gln Gly Gly Asp Asp Val Phe Lys Glu Asn Tyr Val

721 Thr Leu Ser Gly Thr Phe Asp Glu Cys Tyr Pro Thr Tyr Leu Tyr
736 Gln Lys Ile Asp Glu Ser Lys Leu Lys Ala Phe Thr Arg Tyr Gln
751 Leu Arg Gly Tyr Ile Glu Asp Ser Gln Asp Leu Glu Ile Tyr Leu
766 Ile Arg Tyr Asn Ala Lys His Glu Thr Val Asn Val Pro Gly Thr
781 Gly Ser Leu Trp Pro Leu Ser Ala Gln Ser Pro Ile Gly Lys Cys
796 Gly Glu Pro Asn Arg Cys Ala Pro His Leu Glu Trp Asn Pro Asp
811 Leu Asp Cys Ser Cys Arg Asp Gly Glu Lys Cys Ala His His Ser
826 His His Phe Ser Leu Asp Ile Asp Val Gly Cys Thr Asp Leu Asn
841 Glu Asp Leu Gly Val Trp Val Ile Phe Lys Ile Lys Thr Gln Asp
856 Gly His Ala Arg Leu Gly Asn Leu Glu Phe Leu Glu Glu Lys Pro
871 Leu Val Gly Glu Ala Leu Ala Arg Val Lys Arg Ala Glu Lys Lys
886 Trp Arg Asp Lys Arg Glu Lys Leu Glu Trp Glu Thr Asn Ile Val
901 Tyr Lys Glu Ala Lys Glu Ser Val Asp Ala Leu Phe Val Asn Ser
916 Gln Tyr Asp Gln Leu Gln Ala Asp Thr Asn Ile Ala Met Ile His
931 Ala Ala Asp Lys Arg Val His Ser Ile Arg Glu Ala Tyr Leu Pro
946 Glu Leu Ser Val Ile Pro Gly Val Asn Ala Ala Ile Phe Glu Glu
961 Leu Glu Gly Arg Ile Phe Thr Ala Phe Ser Leu Tyr Asp Ala Arg

976 Asn Val Ile Lys Asn Gly Asp Phe Asn Asn Gly Leu Ser Cys Trp
991 Asn Val Lys Gly His Val Asp Val Glu Glu Gln Asn Asn Gln Arg
1006 Ser Val Leu Val Val Pro Glu Trp Glu Ala Glu Val Ser Gln Glu
1021 Val Arg Val Cys Pro Gly Arg Gly Tyr Ile Leu Arg Val Thr Ala
1036 Tyr Lys Glu Gly Tyr Gly Glu Gly Cys Val Thr Ile His Glu Ile
1051 Glu Asn Asn Thr Asp Glu Leu Lys Phe Ser Asn Cys Val Glu Glu
1066 Glu Ile Tyr Pro Asn Asn Thr Val Thr Cys Asn Asp Tyr Thr Val
1081 Asn Gln Glu Glu Tyr Gly Gly Ala Tyr Thr Ser Arg Asn Arg Gly
1096 Tyr Asn Glu Ala Pro Ser Val Pro Ala Asp Tyr Ala Ser Val Tyr
1111 Glu Glu Lys Ser Tyr Thr Asp Gly Arg Arg Glu Asn Pro Cys Glu
1126 Phe Asn Arg Gly Tyr Arg Asp Tyr Thr Pro Leu Pro Val Gly Tyr
1141 Val Thr Lys Glu Leu Glu Tyr Phe Pro Glu Thr Asp Lys Val Trp
1156 Ile Glu Ile Gly Glu Thr Glu Gly Thr Phe Ile Val Asp Ser Val
1171 Glu Leu Leu Leu Met Glu Glu

Fragment 1-*
```

A. B.t. PS81GG uncut
B. B.t. PS81GG cut with HindIII
C. B.t. HD-1 uncut
D. B.t. HD-1 cut with HindIII

A  B  C  D

```
      10         20         30         40         50         60
  1 ATGGATAACA ATCCGAACAT CAATGAATGC ATTCCTTATA ATTGTTTAAG TAACCCTGAA
 61 GTAGAAGTAT TAGGTGGAGA AAGAATAGAA ACTGGTTACA CCCCAATCGA TATTTCCTTG
121 TCGCTAACGC AATTTCTTTT GAGTGAATTT GTTCCCGGTG CTGGATTTGT GTTAGGACTA
181 GTTGATATAA TATGGGGAAT TTTTGGTCCC TCTCAATGGG ACGCATTTCT TGTACAAATT
241 GAACAGTTAA TTAACCAAAG AATAGAAGAA TTCGCTAGGA ACCAAGCCAT TTCTAGATTA 310        320        330        340        350        360
301 GAAGGACTAA GCAATCTTTA TCAAATTTAC GCAGAATCTT TTAGAGAGTG GGAAGCAGAT
361 CCTACTAATC CAGCATTAAG AGAAGAGATG CGTATTCAAT TCAATGACAT GAACAGTGCC
421 CTTACAACCG CTATTCCTCT TTTGGCAGTT CAAATTATC AAGTTCCTCT TTTATCAGTA
481 TATGTTCAAG CTGCAAATTT ACATTATCA GTTTTGAGAG ATGTTTCAGT GTTTGGACAA
541 AGGTGGGAT TGATGCCGC GACTATCAAT AGTCGTTATA ATGATTAAC TAGGCTTATT 610        620        630        640        650        660
601 GGCAACTATA CAGATTATGC TGTACGCTGG TACAATACGG GATTAGAACG TGTATGGGGA
661 CCGGATTCTA GAGATTGGGT AAGGTATAAT CAATTTAGAA GAGAATTAAC ACTAACTGTA
721 TTAGATATCG TTGCTCTGTT CCCGAATTAT TTATACAAAC GATATCCAAT TCGAACAGTT
781 TCCCAATTAA CAAGAGAAAT TTATACAAAC CCAGTATTAG AAAATTTTGA TGGTAGTTTT
841 CGAGGCTCGG CTCAGGGCAT AGAAAGAAGT ATTAGGAGTC CACATTTGAT GGATATACTT
```

FIGURE 2-1

```
              910        920        930        940        950        960
 901 AACAGTATAA CCATCTATAA GGATGCTCAT AGGGGTTATT ATTATTGGTC AGGGCATCAA
 961 ATAATGGCTT CTCCTGTCGG TTTTTCGGGG CCAGAATTCA CGTTTCCGCT ATATGGAACC
1021 ATGGGAAATG CAGCTCCACA ACAACGTATT GTTGCTCAAC TAGGTCAGGG CGTGTATAGA
1081 ACATTATCCT CTACTTTTTA TAGAAGACCT TTTAATATAG GGATAAAATAA TCAACAACTA
1141 TCTGTTCTTG ACGGGACAGA ATTTGCTTAT GGAACCTCCT CAAATTTGCC ATCCGCTGTA 1210       1220       1230       1240       1250       1260
1201 TACAGAAAAA GCGGAACGGT AGATTCGCTG GATGAAAATAC CACCACAGAA TAACAACGTG
1261 CCACCTAGGC AAGGATTAG TCATCGATTA AGCCATGTTT CAATGTTTCG TTCAGGCTCT
1321 AGTAGTAGTG TAAGTATAAT AAGAGCTCCT ATGTTCTCTT GGATACATCG TAGTGCTGAA
1381 TTTAATAATA TAATTGCATC GGATAGTATT ACTCAAATCC CTGCAGTGAA GGGAAACTTT
1441 CTTTTTAATG GTTCTGTAAT TTCAGGACCA GGATTACTG GTGGGGACTT AGTTAGATTA 1510       1520       1530       1540       1550       1560
1501 AATAGTAGTG GAAATAAACAT TCAGAATAGA GGGTATATTG AAGTTCCAAT TCACTTCCCA
1561 TCGACATCTA CCAGATATCG AGTTCGTGTA CGGTATGCTT CTGTAACCCC GATTCACCTC
1621 AACGTTAATT GGGTAATTC TCCAATTTT TCCAATACAG TACCAGCTAC AGCTACGTCA
1681 TTAGATAATC TACAATCAAG TGATTTTGGT TATTTTGAAA GTGCCAATGC TTTTACATCT
1741 TCATTAGGTA ATATAGTAGG TGTTAGAAAT TTTAGTGGGA CTGCAGGAGT GATAATAGAC
```

FIGURE 2-2

```
      1810       1820       1830       1840       1850       1860
1801 AGATTGAAT TTATTCCAGT TACTGCAACA CTCGAGGCTG AATATAATCT GGAAAGAGCG
1861 CAGAAGGCGG TGAATGCGCT GTTTACGTCT ACAAACCAAC TAGGGCTAAA AACAAATGTA
1921 ACGGATTATC ATATTGATCA AGTGTCCAAT TTAGTTACGT ATTTATCGGA TGAATTTGT
1981 CTGGATGAAA AGCGAGAATT GTCCGAGAAA GTCAAACATG CGAAGCGACT CAGTGATGAA
2041 CGCAATTTAC TCCAAGATTC AAATTTCAAA GACATTAATA GGCAACCAGA ACGTGGGTGG 2110       2120       2130       2140       2150       2160
2101 GGCGGAAGTA CAGGGATTAC CATCCAAGGA GGGGATGACG TATTTAAAGA AAATTACGTC
2161 ACACTATCAG GTACCTTTGA TGAGTGCTAT CCAACATATT TGTATCAAAA AATCGATGAA
2221 TCAAAATTAA AAGCCTTTAC CCGTTATCAA TTAAGAGGGT ATATCGAAGA TAGTCAAGAC
2281 TTAGAAATCT ATTTAATTCG CTACACAATGCA AAACATGAAA CAGTAAATGT GCCAGGTACG
2341 GGTTCCTTAT GGCCGCTTTC AGCCCAAAGT CCAATCGGAA AGTGTGGAGA GCCGAATCGA 2410       2420       2430       2440       2450       2460
2401 TGCGCGCCAC ACCTTGAATG GAATCCTGAC TTAGATTGTT CGTGTAGGGA TGGAGAAAAG
2461 TGTGCCCATC ATTCGCATCA TTTCTCCTTA GACATTGATG TAGGATGTAC AGACTTAAAT
2521 GAGGACCTAG GTGTATGGGT GATCTTTAAG ATTAAGACGC AAGATGGGCA CGCAAGACTA
2581 GGGAATCTAG AGTTTCTCGA AGAGAAACCA TTAGTAGGAG AAGCGCTAGC TCGTGTGAAA
2641 AGAGCGGAGA AAAAATGGAG AGACAAACGT GAAAATTGG AATGGGAAAC AAATATCGTT
```

FIGURE 2-3

```
          2710       2720       2730       2740       2750       2760
2701 TATAAAGAGG CAAAAGAATC TGTAGATGCT TTATTTGTAA ACTCTCAATA TGATCAATTA
2761 CAAGCGGATA CGAATATTGC CATGATTCAT GCGGCAGATA AACGTGTTCA TAGCATTCGA
2821 GAAGCTTATC TGCCTGAGCT GTCTGTGATT CCGGGTGTCA ATGCGGCTAT TTTTGAAGAA
2881 TTAGAAGGGC GTATTTCAC TGCATTCTCC CTATATGATG CGAGAAATGT CATTAAAAAT
2941 GGTGATTTTA ATAATGGCTT ATCCTGCTGG AACGTGAAAG GGCATGTAGA TGTAGAAGAA 3010       3020       3030       3040       3050       3060
3001 CAAAACAACC AACGTTCGGT CCTTGTTGTT CCGGAATGGG AAGCAGAAGT GTCACAAGAA
3061 GTTCGTGTCT GTCCGGGTCG TGGCTATATC CTTCGTGTCA CAGCGTACAA GGAGGATAT
3121 GGAGAAGGTT GCGTAACCAT TCATGAGATC GAGAACAATA CAGACGAACT GAAGTTTAGC
3181 AACTGCGTAG AAGAGAAAT CTATCCAAAT AACACGGTAA CGTGTAATGA TTATACTGTA
3241 AATCAAGAAG AATACGGAGG TGCGTACACT TCTCGTAATC GAGGATATAA CGAAGCTCCT 3310       3320       3330       3340       3350       3360
3301 TCCGTACCAG CTGATTATGC GTCAGTCTAT GAAGAAAAAT CGTATACAGA TGGACGAAGA
3361 GAGAATCCTT GTGAATTTAA CAGAGGGTAT AGGGATTACA CGCCACTACC AGTTGGTTAT
3421 GTGACAAAAG AATTAGAATA CTTCCCAGAA ACCGATAAGG TATGGATTGA GATTGGAGAA
3481 ACGGAAGGAA CATTTATCGT GGACAGCGTG GAATTACTCC TTATGGAGGA A*

Segment 1-3531

FIGURE 2-4
```

|     | 1   |     |     |     | 5   |     |     |     |     | 10  |     |     |     |     | 15  |
| --- | --- | --- | --- | --- | --- | --- | --- | --- | --- | --- | --- | --- | --- | --- | --- |
| 1   | Met | Asp | Asn | Asn | Pro | Asn | Ile | Asn | Glu | Cys | Ile | Pro | Tyr | Asn | Cys |
| 16  | Leu | Ser | Asn | Pro | Glu | Val | Glu | Val | Leu | Gly | Gly | Glu | Arg | Ile | Glu |
| 31  | Thr | Gly | Tyr | Thr | Pro | Ile | Asp | Ile | Ser | Leu | Ser | Leu | Thr | Gln | Phe |
| 46  | Leu | Leu | Ser | Glu | Phe | Val | Pro | Gly | Ala | Gly | Phe | Val | Leu | Gly | Leu |
| 61  | Val | Asp | Ile | Ile | Trp | Gly | Ile | Phe | Gly | Pro | Ser | Gln | Trp | Asp | Ala |
| 76  | Phe | Leu | Val | Gln | Ile | Glu | Gln | Leu | Ile | Asn | Gln | Arg | Ile | Glu | Glu |
| 91  | Phe | Ala | Arg | Asn | Gln | Ala | Ile | Ser | Arg | Leu | Glu | Gly | Leu | Ser | Asn |
| 106 | Leu | Tyr | Gln | Ile | Tyr | Ala | Glu | Ser | Phe | Arg | Glu | Trp | Glu | Ala | Asp |
| 121 | Pro | Thr | Asn | Pro | Ala | Leu | Arg | Glu | Glu | Met | Arg | Ile | Gln | Phe | Asn |
| 136 | Asp | Met | Asn | Ser | Ala | Leu | Thr | Thr | Ala | Ile | Pro | Leu | Leu | Ala | Val |
| 151 | Gln | Asn | Tyr | Gln | Val | Pro | Leu | Leu | Ser | Val | Tyr | Val | Gln | Ala | Ala |
| 166 | Asn | Leu | His | Leu | Ser | Val | Leu | Arg | Asp | Val | Ser | Val | Phe | Gly | Gln |
| 181 | Arg | Trp | Gly | Phe | Asp | Ala | Ala | Thr | Ile | Asn | Ser | Arg | Tyr | Asn | Asp |
| 196 | Leu | Thr | Arg | Leu | Ile | Gly | Asn | Tyr | Thr | Asp | Tyr | Ala | Val | Arg | Trp |
| 211 | Tyr | Asn | Thr | Gly | Leu | Glu | Arg | Val | Trp | Gly | Pro | Asp | Ser | Arg | Asp |
| 226 | Trp | Val | Arg | Tyr | Asn | Gln | Phe | Arg | Arg | Glu | Leu | Thr | Leu | Thr | Val |

FIGURE 3-1

| 241 | Leu | Asp | Ile | Val | Ala | Leu | Phe | Pro | Asn | Tyr | Asp | Ser | Arg | Arg | Tyr |
|---|---|---|---|---|---|---|---|---|---|---|---|---|---|---|---|
| 256 | Pro | Ile | Arg | Thr | Val | Ser | Gln | Leu | Thr | Arg | Glu | Ile | Tyr | Thr | Asn |
| 271 | Pro | Val | Leu | Glu | Asn | Phe | Asp | Gly | Ser | Phe | Arg | Gly | Ser | Ala | Gln |
| 286 | Gly | Ile | Glu | Arg | Ser | Ile | Arg | Ser | Pro | His | Leu | Met | Asp | Ile | Leu |
| 301 | Asn | Ser | Ile | Thr | Ile | Tyr | Thr | Asp | Ala | His | Arg | Gly | Tyr | Tyr | Tyr |
| 316 | Trp | Ser | Gly | His | Gln | Ile | Met | Ala | Ser | Pro | Val | Gly | Phe | Ser | Gly |
| 331 | Pro | Glu | Phe | Thr | Phe | Pro | Leu | Tyr | Gly | Thr | Met | Gly | Asn | Ala | Ala |
| 346 | Pro | Gln | Arg | Ile | Val | Ala | Gln | Leu | Gly | Gln | Gly | Val | Tyr | Arg |
| 361 | Thr | Leu | Ser | Ser | Thr | Phe | Tyr | Arg | Arg | Pro | Phe | Asn | Ile | Gly | Ile |
| 376 | Asn | Gln | Gln | Leu | Ser | Val | Leu | Asp | Gly | Thr | Glu | Phe | Ala | Tyr |
| 391 | Gly | Thr | Ser | Ser | Asn | Leu | Pro | Ser | Ala | Val | Tyr | Arg | Lys | Ser | Gly |
| 406 | Thr | Val | Asp | Ser | Leu | Asp | Glu | Ile | Pro | Pro | Gln | Asn | Asn | Asn | Val |
| 421 | Pro | Pro | Arg | Gln | Gly | Phe | Ser | His | Arg | Leu | Ser | His | Val | Ser | Met |
| 436 | Phe | Arg | Ser | Gly | Phe | Ser | Ser | Ser | Val | Ser | Ile | Ile | Arg | Ala | Pro |
| 451 | Met | Phe | Ser | Trp | Ile | His | Arg | Ser | Ala | Glu | Phe | Asn | Asn | Ile | Ile |
| 466 | Ala | Ser | Asp | Ser | Ile | Thr | Gln | Ile | Pro | Ala | Val | Lys | Gly | Asn | Phe |

FIGURE 3-2

```
481  Leu Phe Asn Gly Ser Val Ile Ser Gly Pro Gly Phe Thr Gly Gly
496  Asp Leu Arg Leu Asn Ser Ser Gly Asn Ser Ile Gln Asn Arg
511  Gly Tyr Ile Glu Val Pro Ile His Phe Pro Ser Thr Ser Thr Arg
526  Tyr Arg Val Arg Val Arg Tyr Ala Ser Val Thr Pro Ile His Leu
541  Asn Val Asn Trp Gly Asn Ser Ser Ile Phe Ser Asn Thr Val Pro
556  Ala Thr Ala Thr Ser Leu Asp Asn Leu Gln Ser Ser Asp Phe Gly
571  Tyr Phe Glu Ser Ala Asn Ala Phe Thr Ser Ser Leu Gly Asn Ile
586  Val Gly Val Arg Asn Phe Ser Gly Thr Ala Gly Val Ile Ile Asp
601  Arg Phe Glu Phe Ile Pro Val Thr Ala Thr Leu Glu Ala Glu Tyr
616  Asn Leu Glu Arg Ala Gln Lys Ala Val Asn Ala Leu Phe Thr Ser
631  Thr Asn Gln Leu Gly Leu Lys Thr Asn Val Thr Asp Tyr His Ile
646  Asp Gln Val Ser Asn Leu Val Thr Tyr Leu Ser Asp Glu Phe Cys
661  Leu Asp Glu Lys Arg Glu Leu Ser Glu Lys Val Lys His Ala Lys
676  Arg Leu Ser Asp Glu Arg Asn Leu Leu Gln Asp Ser Asn Phe Lys
691  Asp Ile Asn Arg Gln Pro Glu Arg Gly Trp Gly Gly Ser Thr Gly
706  Ile Thr Ile Gln Gly Gly Asp Asp Val Phe Lys Glu Asn Tyr Val
```

FIGURE 3-3

| 721 | Thr | Leu | Ser | Gly | Thr | Phe | Asp | Glu | Cys | Tyr | Pro | Thr | Tyr | Leu | Tyr |
| --- | --- | --- | --- | --- | --- | --- | --- | --- | --- | --- | --- | --- | --- | --- | --- |
| 736 | Gln | Lys | Ile | Asp | Glu | Ser | Lys | Leu | Lys | Ala | Phe | Thr | Arg | Tyr | Gln |
| 751 | Leu | Arg | Gly | Tyr | Ile | Glu | Asp | Ser | Gln | Asp | Leu | Glu | Ile | Tyr | Leu |
| 766 | Ile | Arg | Ala | Asn | Ala | Lys | His | Glu | Thr | Val | Asn | Val | Pro | Gly | Thr |
| 781 | Gly | Ser | Leu | Trp | Pro | Leu | Ser | Ala | Gln | Ser | Pro | Ile | Gly | Lys | Cys |
| 796 | Gly | Glu | Pro | Asn | Arg | Cys | Ala | Pro | His | Leu | Glu | Trp | Asn | Pro | Asp |
| 811 | Leu | Asp | Cys | Ser | Arg | Asp | Gly | Gly | Glu | Lys | Cys | Ala | His | His | Ser |
| 826 | His | His | Phe | Ser | Leu | Asp | Ile | Asp | Val | Gly | Cys | Thr | Asp | Leu | Asn |
| 841 | Glu | Asp | Leu | Gly | Val | Trp | Val | Ile | Phe | Lys | Ile | Lys | Thr | Gln | Asp |
| 856 | Gly | His | Ala | Arg | Leu | Gly | Asn | Leu | Glu | Phe | Leu | Glu | Glu | Lys | Pro |
| 871 | Leu | Val | Gly | Glu | Ala | Leu | Ala | Arg | Val | Lys | Arg | Ala | Glu | Ile | Lys |
| 886 | Trp | Arg | Asp | Lys | Arg | Glu | Lys | Leu | Glu | Trp | Glu | Thr | Asn | Ile | Val |
| 901 | Tyr | Lys | Glu | Ala | Lys | Glu | Ser | Val | Asp | Ala | Leu | Phe | Val | Asn | Ser |
| 916 | Gln | Tyr | Asp | Gln | Leu | Gln | Ala | Asp | Thr | Asn | Ile | Ala | Met | Ile | His |
| 931 | Ala | Ala | Asp | Lys | Arg | Val | His | Ser | Ile | Arg | Glu | Ala | Tyr | Leu | Pro |
| 946 | Glu | Leu | Ser | Val | Ile | Pro | Gly | Val | Asn | Ala | Ala | Ile | Phe | Glu | Glu |
| 961 | Leu | Glu | Gly | Arg | Ile | Phe | Thr | Ala | Phe | Ser | Leu | Tyr | Asp | Ala | Arg |

FIGURE 3-4

```
 976 Asn Val Ile Lys Asn Gly Asp Phe Asn Asn Gly Leu Ser Cys Trp
 991 Asn Val Lys Gly His Val Asp Val Glu Gln Asn Asn Ser Gln Arg
1006 Ser Val Leu Val Pro Glu Trp Glu Ala Glu Val Val Ser Gln Glu
1021 Val Arg Val Cys Pro Gly Arg Gly Ile Tyr Ile Arg Val Thr Ala
1036 Tyr Lys Glu Gly Tyr Gly Gly Leu Cys Val Leu Arg Ile His Glu
1051 Glu Asn Asn Thr Asp Lys Leu Ser Phe Ser Val Cys Val Glu Glu
1066 Glu Ile Tyr Pro Asn Asn Thr Val Thr Cys Asn Asp Tyr Thr Val
1081 Asn Gln Glu Tyr Gly Gly Ala Tyr Thr Ser Arg Asn Arg Gly Tyr
1096 Tyr Asn Glu Ala Pro Ser Val Pro Ala Asp Tyr Ala Ser Val Tyr
1111 Glu Glu Lys Ser Tyr Thr Asp Gly Arg Glu Glu Asn Pro Cys Glu
1126 Phe Asn Arg Gly Tyr Tyr Arg Asp Tyr Thr Pro Leu Pro Val Gly Tyr
1141 Val Thr Lys Glu Leu Glu Tyr Phe Pro Glu Thr Asp Lys Val Trp
1156 Ile Glu Ile Leu Gly Thr Glu Pro Gly Ile Val Asp Ser Val
1171 Glu Leu Leu Met Glu Glu
```

Fragment 1–*

FIGURE 3-5

```
            5                   10                  15                  20
Met Asp Asn Asn Pro Asn Ile Asn Glu Cys Ile Pro Tyr Asn Cys Leu Ser Asn Pro Glu
ATG GAT AAC AAT CCG AAC ATC AAT GAA TGC ATT CCT TAT AAT TGT TTA AGT AAC CCT GAA 25                  30                  35                  40
Val Glu Val Leu Gly Gly Glu Arg Ile Glu Thr Gly Tyr Thr Pro Ile Asp Ile Ser Leu
GTA GAA GTA TTA GGT GGA GAA AGA ATA GAA ACT GGT TAC ACC CCA ATC GAT ATT TCC TTG 45                  50                  55                  60
Ser Leu Thr Gln Phe Leu Leu Ser Glu Phe Val Pro Gly Ala Gly Phe Val Leu Gly Leu
TCG CTA ACG CAA TTT CTT TTG AGT GAA TTT GTT CCC GGT GCT GGA TTT GTG TTA GGA CTA 65                  70                  75                  80
Val Asp Ile Ile Trp Gly Ile Phe Gly Pro Ser Gln Trp Asp Ala Phe Leu Val Gln Ile
GTT GAT ATA ATA TGG GGA ATT TTT GGT CCC TCT CAA TGG GAC GCA TTT CTT GTA CAA ATT
```

FIGURE 4-1

|  |  | 85 |  |  |  | 90 |  |  |  | 95 |  |  |  | 100 |
|---|---|---|---|---|---|---|---|---|---|---|---|---|---|---|
| Glu | Gln | Leu | Ile | Asn | Gln | Arg | Ile | Glu | Phe | Ala | Arg | Asn | Gln | Ala | Ile | Ser | Arg | Leu |
| GAA | CAG | TTA | ATT | AAC | CAA | AGA | ATA | GAA | TTC | GCT | AGG | AAC | CAA | GCC | ATT | TCT | AGA | TTA |

|  |  | 105 |  |  |  | 110 |  |  |  | 115 |  |  |  | 120 |
| Glu | Gly | Leu | Ser | Asn | Leu | Tyr | Ala | Ile | Tyr | Gln | Ile | Ser | Phe | Arg | Glu | Trp | Glu | Ala | Asp |
| GAA | GGA | CTA | AGC | AAT | CTT | TAT | GCA | ATT | TAC | CAA | TCT | TTT | AGA | GAG | TGG | GAA | GCA | GAT |

|  |  | 125 |  |  |  | 130 |  |  |  | 135 |  |  |  | 140 |
| Pro | Thr | Asn | Pro | Ala | Leu | Arg | Glu | Glu | Met | Arg | Ile | Gln | Phe | Asn | Asp | Met | Asn | Ser | Ala |
| CCT | ACT | AAT | CCA | GCA | TTA | AGA | GAA | GAG | ATG | CGT | ATT | CAA | TTC | AAT | GAC | ATG | AAC | AGT | GCC |

|  |  | 145 |  |  |  | 150 |  |  |  | 155 |  |  |  | 160 |
| Leu | Thr | Thr | Ala | Ile | Pro | Leu | Leu | Ala | Val | Gln | Asn | Tyr | Gln | Val | Pro | Leu | Leu | Ser | Val |
| CTT | ACA | ACC | GCT | ATT | CCT | CTT | TTG | GCA | GTT | CAA | AAT | TAT | CAA | GTT | CCT | CTT | TTA | TCA | GTA |

FIGURE 4-2

```
                                         175                    180
Tyr Val Gln Ala Ala Asn Leu His Leu Ser Val Leu Arg Asp Val Ser Val Phe Gly Gln
TAT GTT CAA GCT GCA AAT TTA CAT TTA TCA GTT TTG AGA GAT GTT TCA GTG TTT GGA CAA 195                    200
Arg Trp Gly Phe Asp Ala Ala Thr Ile Asn Ser Arg Tyr Asn Asp Leu Thr Arg Leu Ile
AGG TGG GGA TTT GAT GCC GCG ACT ATC AAT AGT CGT TAT AAT GAT TTA ACT AGG CTT ATT 215                    220
Gly Asn Tyr Thr Asp Tyr Ala Val Arg Trp Tyr Asn Thr Gly Leu Glu Arg Val Trp Gly
GGC AAC TAT ACA GAT TAT GCT GTA CGC TGG TAC AAT ACG GGA TTA GAA CGT GTA TGG GGA 235                    240
Pro Asp Ser Arg Asp Trp Val Arg Tyr Asn Gln Phe Arg Arg Glu Leu Thr Leu Thr Val
CCG GAT TCT AGA GAT TGG GTA AGG TAT AAT CAA TTT AGA AGA GAA TTA ACA CTA ACT GTA
```

FIGURE 4-3

|     | 245 |     |     |     | 250 |     |     |     | 255 |     |     |     | 260 |
| --- | --- | --- | --- | --- | --- | --- | --- | --- | --- | --- | --- | --- | --- |
| Leu | Asp | Ile | Val | Ala | Leu | Phe | Pro | Asn | Tyr | Asp | Ser | Arg | Arg | Tyr | Pro | Ile | Arg | Thr | Val |
| TTA | GAT | ATC | GTT | GCT | CTG | TTC | CCG | AAT | TAT | GAT | AGT | AGA | AGA | TAT | CCA | ATT | CGA | ACA | GTT |

|     |     |     |     | 265 |     |     |     |     | 270 |     |     |     |     | 275 |     |     |     |     | 280 |
| --- | --- | --- | --- | --- | --- | --- | --- | --- | --- | --- | --- | --- | --- | --- | --- | --- | --- | --- | --- |
| Ser | Gln | Leu | Thr | Arg | Glu | Ile | Tyr | Thr | Asn | Pro | Val | Leu | Glu | Asn | Phe | Asp | Gly | Ser | Phe |
| TCC | CAA | TTA | ACA | AGA | GAA | ATT | TAT | ACA | AAC | CCA | GTA | TTA | GAA | AAT | TTT | GAT | GGT | AGT | TTT |

|     |     |     |     | 285 |     |     |     |     | 290 |     |     |     |     | 295 |     |     |     |     | 300 |
| --- | --- | --- | --- | --- | --- | --- | --- | --- | --- | --- | --- | --- | --- | --- | --- | --- | --- | --- | --- |
| Arg | Gly | Ser | Ala | Gln | Gly | Ile | Glu | Arg | Ser | Ile | Arg | Ser | Pro | His | Leu | Met | Asp | Ile | Leu |
| CGA | GGC | TCG | GCT | CAG | GGC | ATA | GAA | AGA | AGT | ATT | AGG | AGT | CCA | CAT | TTG | ATG | GAT | ATA | CTT |

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |
| Asn | Ser | Ile | Thr | Ile | Tyr | Thr | Asp | Ala | His | Arg | Gly | Tyr | Tyr | Tyr | Trp | Ser | Gly | His | Gln |
| AAC | AGT | ATA | ACC | TAT | ACG | GAT | GCT | CAT | AGG | GGT | TAT | TAT | TAT | TGG | TCA | GGG | CAT | CAA |

FIGURE 4-4

```
                                325             330             335             340
Ile Met Ala Ser Pro Val Gly Phe Ser Gly Pro Glu Phe Thr Pro Leu Tyr Gly Thr
ATA ATG GCT TCT CCT GTC GGT TTT TCG GGG CCA GAA TTC ACG CCG CTA TAT GGA ACC 345             350             355             360
Met Gly Asn Ala Ala Pro Gln Gln Arg Ile Val Ala Gln Leu Gly Gln Gly Val Tyr Arg
ATG GGA AAT GCA GCA CCA CAA CAA CGT ATT GTT GCT CAA CTA GGT CAG GGC GTG TAT AGA 365             370             375             380
Thr Leu Ser Ser Thr Phe Tyr Arg Arg Pro Phe Asn Ile Gly Ile Asn Asn Gln Gln Leu
ACA TTA TCC TCT ACT TTT TAT AGA AGA CCT TTT AAT ATA GGG ATA AAT AAT CAA CAA CTA 385             390             395             400
Ser Val Leu Asp Gly Thr Glu Phe Ala Tyr Gly Thr Ser Ser Asn Leu Pro Ser Ala Val
TCT GTT CTT GAC GGG ACA GAA TTT GCT TAT GGA ACC TCC TCA AAT TTG CCA TCC GCT GTA
```

FIGURE 4-5

```
                405             410             415             420
Tyr Arg Lys Ser Gly Thr Val Asp Ser Leu Asp Glu Ile Pro Gln Asn Asn Val
TAC AGA AAA AGC GGA ACG GTA GAT TCG CTG GAT GAA ATA CCA CAG AAT AAC GTG 425             430             435             440
Pro Pro Arg Gln Gly Phe Ser His Arg Leu Ser His Val Ser Met Phe Arg Ser Gly Ser
CCA CCT AGG CAA GGA TTT AGT CAT CGA TTA AGC CAT GTT TCA ATG TTT CGT TCA GGC TCT 445             450             455             460
Ser Ser Val Ser Ile Ile Arg Ala Pro Met Phe Ser Trp Ile His Arg Ser Ala Glu
AGT AGT GTA AGT ATA ATA AGA GCT CCT ATG TTC TCT TGG ATA CAT CGT AGT GCT GAA 465             470             475             480
Phe Asn Asn Ile Ile Ala Ser Asp Ser Ile Thr Gln Ile Pro Ala Val Lys Gly Asn Phe
TTT AAT AAT ATA ATT GCA TCG GAT AGT ATT ACT CAA ATC CCT GCA GTG AAG GGA AAC TTT
```

FIGURE 4-6

```
                                      485                    490                    495                    500
Leu Phe Asn Gly Ser Val Ile Ser Gly Pro Gly Phe Thr Gly Asp Leu Val Arg Leu
CTT TTT AAT GGT TCT GTA ATT TCA GGA CCA GGA TTT ACT GGT GAC TTA GTT AGA TTA 505                    510                    515                    520
Asn Ser Gly Asn Ile Gln Asn Ile Gly Tyr Ile Glu Val Pro Ile His Phe Pro
AAT AGT AGT GGA AAT ATT CAG AAT ATT GGG TAT ATT GAA GTT CCA ATT CAC TTC CCA 525                    530                    535                    540
Ser Thr Ser Arg Tyr Arg Val Arg Tyr Ala Ser Val Thr Pro Ile His Leu
TCG ACA TCT AGA TAT CGA GTT CGT TAT GCT TCT GTA ACC CCG ATT CAC CTC 545                    550                    555                    560
Asn Val Asn Trp Gly Asn Ser Ser Ile Phe Ser Asn Thr Val Pro Ala Thr Ala Thr Ser
AAC GTT AAT TGG GGT AAT TCA TCC ATT TTT TCC AAT ACA GTA CCA GCT ACA ACG TCA 565                    570                    575                    580
Leu Asp Asn Leu Gln Ser Ser Asp Phe Gly Tyr Phe Glu Ser Ala Asn Ala Phe Thr Ser
TTA GAT AAT CTA CAA TCA AGT GAT TTT GGT TAT TTT GAA AGT GCC AAT GCT TTT ACA TCT
```

FIGURE 4-7

```
                            585                    590                595                    600
Ser Leu Gly Asn Ile Val Gly Val Arg Asn Phe Ser Gly Thr Ala Gly Val Ile Ile Asp
TCA TTA GGT AAT ATA GTA GGT GTT AGA AAT TTT AGT GGG ACT GCA GGA GTG ATA ATA GAC
                            605                    610                615                    620
Arg Phe Glu Phe Ile Pro Val Thr Ala Leu Thr Leu Glu Ala Glu Tyr Asn Leu Glu Arg Ala
AGA TTT GAA TTT ATT CCA GTT ACT GCA CTC GAG GCT GAA TAT AAT CTG GAA AGA GCG
                            625                    630                635                    640
Gln Lys Ala Val Asn Ala Leu Phe Thr Ser Thr Asn Gln Leu Gly Leu Lys Thr Asn Val
CAG AAG GCG GTG AAT GCG CTG TTT ACG TCT ACA AAC CAA CTA GGG CTA AAA ACA AAT GTA
                            645                    650                655                    660
Thr Asp Tyr His Ile Asp Gln Val Ser Asn Leu Val Thr Tyr Leu Ser Asp Glu Phe Cys
ACG GAT TAT CAT ATT GAT CAA GTG TCC AAT TTA GTT ACG TAT TTA TCG GAT GAA TTT TGT
```

FIGURE 4-8

```
                        665                 670                 675                 680
Leu Asp Glu Lys Arg Glu Lys Leu Ser Glu Lys Val Lys His Ala Lys Arg Leu Ser Asp Glu
CTG GAT GAA AAG CGA GAA TTG TCC GAG AAA GTC AAA CAT GCG AAG CGA CTC AGT GAT GAA 685                 690                 695                 700
Arg Asn Leu Leu Gln Asp Ser Asn Phe Lys Asp Ile Asn Arg Gln Pro Glu Arg Gly Trp
CGC AAT TTA CTC CAA GAT TCA AAT TTC AAA GAC ATT AAT AGG CAA CCA GAA CGT GGG TGG 705                 710                 715                 720
Gly Gly Ser Thr Gly Ile Gly Ile Thr Ile Gln Gly Gly Asp Val Phe Lys Glu Asn Tyr Val
GGC GGA AGT ACA GGG ATT ACC ATC CAA GGA GAT GAC GTA TTT AAA GAA AAT TAC GTC 725                 730                 735                 740
Thr Leu Ser Gly Thr Phe Asp Glu Cys Tyr Pro Thr Tyr Leu Tyr Gln Lys Ile Asp Glu
ACA CTA TCA GGT ACC TTT GAT GAG TGC TAT CCA ACA TAT TTG TAT CAA AAA ATC GAT GAA
```

FIGURE 4-9

```
                745                  750                  755                  760
Ser Lys Leu Lys Ala Phe Thr Arg Tyr Gln Leu Arg Gly Tyr Ile Glu Asp Ser Gln Asp
TCA AAA TTA AAA GCC TTT ACC CGT TAT CAA TTA AGA GGG TAT ATC GAA GAT AGT CAA GAC 765                  770                  775                  780
Leu Glu Ile Tyr Leu Ile Arg Tyr Asn Ala Lys His Glu Thr Val Asn Val Pro Gly Thr
TTA GAA ATC TAT TTA ATT CGC TAC AAT GCA AAA CAT GAA ACA GTA AAT GTG CCA GGT ACG 785                  790                  795                  800
Gly Ser Leu Trp Pro Leu Ser Ala Gln Ser Pro Ile Gly Lys Cys Gly Glu Pro Asn Arg
GGT TCC TTA TGG CCG CTT TCA GCC CAA AGT CCA ATC GGA AAG TGT GGA GAG CCG AAT CGA 805                  810                  815                  820
Cys Ala Pro His Leu Glu Trp Asn Pro Asp Leu Asp Cys Ser Cys Arg Asp Gly Glu Lys
TGC GCG CCA CAC CTT GAA TGG AAT CCT GAC TTA GAT TGT TCG TGT AGG GAT GGA GAA AAG

FIGURE 4-10
```

```
                825             830             835             840
Cys Ala His His Ser His His Phe Ser Leu Asp Ile Asp Val Gly Cys Thr Asp Leu Asn
TGT GCC CAT CAT TCG CAT CAT TTC TCC TTA GAC ATT GAT GTA GGA TGT ACA GAC TTA AAT 845             850             855             860
Glu Asp Leu Gly Val Ile Trp Val Ile Phe Lys Thr Gln Ile Asp Gly His Ala Arg Leu
GAG GAC CTA GGT GTA ATC TGG GTG ATC TTT AAG ACG CAA GAT GGG CAC GCA AGA CTA 865             870             875             880
Gly Asn Leu Glu Phe Leu Glu Lys Pro Leu Val Gly Glu Leu Ala Arg Val Lys
GGG AAT CTA GAG TTT CTC GAA GAG AAA CCA TTA GTA GGA GAA GCG CTA GCT CGT GTG AAA 885             890             895             900
Arg Ala Glu Lys Lys Trp Arg Asp Lys Arg Glu Lys Leu Glu Trp Glu Thr Asn Ile Val
AGA GCG GAG AAA AAA TGG AGA GAC AAA CGT GAA AAA TTG GAA TGG GAA ACA AAT ATC GTT
```

FIGURE 4-11

```
                    905                 910                 915                 920
Tyr Lys Glu Ala Lys Glu Ser Val Asp Ala Leu Phe Val Asn Ser Gln Tyr Asp Gln Leu
TAT AAA GAG GCA AAA GAA TCT GTA GAT GCT TTA TTT GTA AAC TCT CAA TAT GAT CAA TTA 925                 930                 935                 940
Gln Ala Asp Thr Asn Ile Ala Met Ile Ala His Ala Ala Asp Lys Arg Val His Ser Ile Arg
CAA GCG GAT ACG AAT ATT GCC ATG ATT GCC CAT GCA GAT AAA CGT GTT CAT AGC ATT CGA 945                 950                 955                 960
Glu Ala Tyr Leu Pro Glu Leu Ser Val Ile Pro Gly Val Asn Ala Ala Ile Phe Glu Glu
GAA GCT TAT CTG CCT GAG CTG TCT GTG ATT CCG GGT GTC AAT GCG GCT ATT TTT GAA GAA 965                 970                 975                 980
Leu Glu Gly Arg Ile Phe Thr Ala Phe Ser Leu Tyr Asp Ala Arg Asn Val Ile Lys Asn
TTA GAA GGG CGT ATT TTC ACT GCA TTC TCC CTA TAT GAT GCG AGA AAT GTC ATT AAA AAT

FIGURE 4-12
```

|     |     |     |     |     | 985 |     |     |     | 990 |     |     |     | 995 |     |     |     | 1000 |     |
| --- | --- | --- | --- | --- | --- | --- | --- | --- | --- | --- | --- | --- | --- | --- | --- | --- | --- | --- |
| Gly | Asp | Phe | Asn | Asn | Gly | Leu | Ser | Cys | Trp | Asn | Val | Lys | Gly | His | Val | Asp | Val | Glu | Glu |
| GGT | GAT | TTT | AAT | AAT | GGC | TTA | TCC | TGC | TGG | AAC | GTG | AAA | GGG | CAT | GTA | GAT | GTA | GAA | GAA |

|     |     |     |     | 1005 |     |     |     | 1010 |     |     |     | 1015 |     |     |     | 1020 |     |     |     |
| --- | --- | --- | --- | --- | --- | --- | --- | --- | --- | --- | --- | --- | --- | --- | --- | --- | --- | --- | --- |
| Gln | Asn | Asn | Gln | Arg | Ser | Val | Leu | Val | Pro | Glu | Trp | Glu | Ala | Glu | Val | Ser | Gln | Glu |
| CAA | AAC | AAC | CAA | CGT | TCG | GTC | CTT | GTT | CCG | GAA | TGG | GAA | GCA | GAA | GTG | TCA | CAA | GAA |

|     |     |     |     | 1025 |     |     |     | 1030 |     |     |     | 1035 |     |     |     | 1040 |     |     |     |
| --- | --- | --- | --- | --- | --- | --- | --- | --- | --- | --- | --- | --- | --- | --- | --- | --- | --- | --- | --- |
| Val | Arg | Val | Cys | Pro | Gly | Arg | Gly | Tyr | Ile | Leu | Arg | Val | Thr | Ala | Tyr | Lys | Glu | Gly | Tyr |
| GTT | CGT | GTC | TGT | CCG | GGT | CGT | GGC | TAT | ATC | CTT | CGT | GTC | ACA | GCG | TAC | AAG | GAG | GGA | TAT |

|     |     |     |     | 1045 |     |     |     | 1050 |     |     |     | 1055 |     |     |     | 1060 |     |     |     |
| --- | --- | --- | --- | --- | --- | --- | --- | --- | --- | --- | --- | --- | --- | --- | --- | --- | --- | --- | --- |
| Gly | Gly | Cys | Val | Thr | Ile | His | Glu | Ile | Glu | Asn | Asn | Thr | Asp | Glu | Leu | Lys | Phe | Ser |
| GGA | GAA | GGT | TGC | GTA | ACC | ATT | CAT | GAG | ATC | GAG | AAC | AAT | ACA | GAC | GAA | CTG | AAG | TTT | AGC |

FIGURE 4-13

```
                        1065                 1070                 1075                 1080
Asn Cys Val Glu Glu Ile Tyr Pro Asn Asn Thr Val Thr Cys Asn Asp Tyr Thr Val
AAC TGC GTA GAA GAG ATC TAT CCA AAT AAC ACG GTA ACG TGT AAT GAT TAT ACT GTA 1085                 1090                 1095                 1100
Asn Gln Glu Glu Tyr Gly Gly Ala Tyr Thr Ser Arg Asn Arg Gly Tyr Asn Glu Ala Pro
AAT CAA GAA GAA TAC GGA GGT GCG TAC ACT TCT CGT AAT CGA GGA TAT AAC GAA GCT CCT 1105                 1110                 1115                 1120
Ser Val Pro Ala Asp Tyr Ala Ser Val Tyr Glu Glu Lys Ser Tyr Thr Asp Gly Arg Arg
TCC GTA CCA GCT GAT TAT GCG TCA GTC TAT GAA GAA AAA TCG TAT ACA GAT GGA CGA AGA 1125                 1130                 1135                 1140
Glu Asn Pro Cys Glu Phe Asn Arg Gly Tyr Arg Asp Tyr Thr Pro Leu Pro Val Gly Tyr
GAG AAT CCT TGT GAA TTT AAC AGA GGG TAT AGG GAT TAC ACG CCA CTA CCA GTT GGT TAT
```

FIGURE 4-14

```
                  1145                1150                1155              1160
Val Thr Lys Glu Leu Glu Tyr Phe Pro Glu Thr Asp Lys Val Trp Ile Glu Ile Gly Glu
GTG ACA AAA GAA TTA GAA TAC TTC CCA GAA ACC GAT AAG GTA TGG ATT GAG ATT GGA GAA 1165                1170                1175
Thr Gly Thr Phe Ile Val Asp Ser Val Glu Leu Leu Leu Met Glu Glu
ACG GGA ACA TTT ATC GTG GAC AGC GTG GAA TTA CTC CTT ATG GAG GAA
```

FIGURE 4-15

GENE ENCODING A LEPIDOPTERAN-ACTIVE TOXIN FROM *BACILLUS THURINGIENSIS* ISOLATE DENOTED *B.T.* PS81GG ACTIVE AGAINST LEPIDOPTERAN PESTS

This is a division of application Ser. No. 07/265,731, filed Nov. 1, 1988.

BACKGROUND OF THE INVENTION (1) Microbial Pesticides

The most widely used microbial pesticides are derived from the bacterium *Bacillus thuringiensis*. This bacterial agent is used to control a wide range of leaf-eating caterpillars, and mosquito *Bacillus thuringiensis* produces a proteinaceous paraspore or crystal which is toxic upon ingestion by a susceptible insect host. For example, *B. thuringiensis* var. *kurstaki* HD-1 produces a crystal called a delta toxin which is toxic to the larvae of a number of lepidopteran insects. The cloning and expression of this *B.t.* crystal protein gene in *Escherichia coli* has been described in the published literature (Schnepf, H. E. and Whitely, H. R. [1981]Proc. Natl. Acad. Sci. USA 78:2893-2897). U.S. Pat. No. 4,448,885 and U.S. Pat. No. 4,467,036 both disclose the expression of *B.t.* crystal protein in *E. coli*.

(2) Lepidopteran Pests

The beet armyworm (BAW) *Spodoptera exiqua* is a widely distributed noctuid moth that attacks a broad range of field and vegetable crops. This economically important species originated in Asia, but is now found in many parts of the world including the United States.

The plants attacked by BAW include beets, peanuts, alfalfa, lettuce, asparagus, tomatoes, potatoes, corn, onions, peas, cotton, citrus, mallow, and even certain wild grasses. It is also a pest on ornamentals and floriculture crops, such as carnations and chrysanthemums. Larvae will feed on the leaves, stems, buds, and sometimes the roots of host plants. Heavy infestations can lead to complete defoliation of fields of a crop, such as table beets.

The female oviposits egg masses of about 80 eggs on the host plant foliage. These egg masses are covered with hairs and scales from the body of the female. An average of 500 g to 600 eggs may be deposited over a 4 to 10 day period Larvae hatch in 2 to 5 days and begin feeding on the foliage. Young larvae will feed in growing tips of the plant and developing buds, while older larvae are less discriminating, feeding on older foliage as well. The five larval instars take about 3 weeks to complete, at which time the mature larva drops to the ground and pupates in the soil. In the warmer parts of its range the BAW passes through four generations per year.

This species is generally considered to be difficult to control in various crop situations. Methomyl (Lannate) is commonly used to control this pest in lettuce and other field crops. However, resistance to methomyl has been reported in populations exposed to heavy use of this chemical (Yoshida and Parella [1987]). Consequently, there is a need to develop alternative control strategies for this important pest.

Another aspect of the use of broad spectrum materials like Lannate for BAW control is secondary pest outbreaks. This is the disruptive influence of a non-selective chemical on natural control agents of other pests in a given crop. In tomatoes, chrysanthemums, and other groups, where leaf miners can be a problem, the use of Lannate severely depresses populations of the natural enemies of the leafminers. With removal of leafminer parasites, the leafminers can build to very high population levels and cause severe damage.

The discovery and use of a novel *Bacillus thuringiensis* isolate with good activity against BAW is a distinct improvement in the control of this lepidopteran pest.

BRIEF SUMMARY OF THE INVENTION

The subject invention concerns a novel *Bacillus thuringiensis* isolate designated *B.t.* PS81GG which has activity against lepidopteran pests. It is highly active against the beet armyworm (BAW).

The subject invention also includes mutants of *B.t.* PS81GG which are also active against lepidopteran pests.

Also disclosed and claimed is the novel toxin gene from the novel isolate. This toxin gene can be transferred to suitable hosts via a plasmid vector.

Specifically, the invention comprises a novel *B.t.* isolate denoted *B.t.* PS81GG, and mutants thereof, and a novel delta endotoxin gene which encodes a 133,156 dalton protein which is active against lepidopteran pests.

BRIEF DESCRIPTION OF THE DRAWING

FIGS. 2-1 through 2-4 show DNA encoding the novel toxin.

FIGS. 3-1 through 3-5 show the amino acid sequence of the novel toxin.

FIGS. 4-1 through 4-15 are a composite of FIGS. 2 and 3.

DETAILED DESCRIPTION OF THE INVENTION

Figure 1:
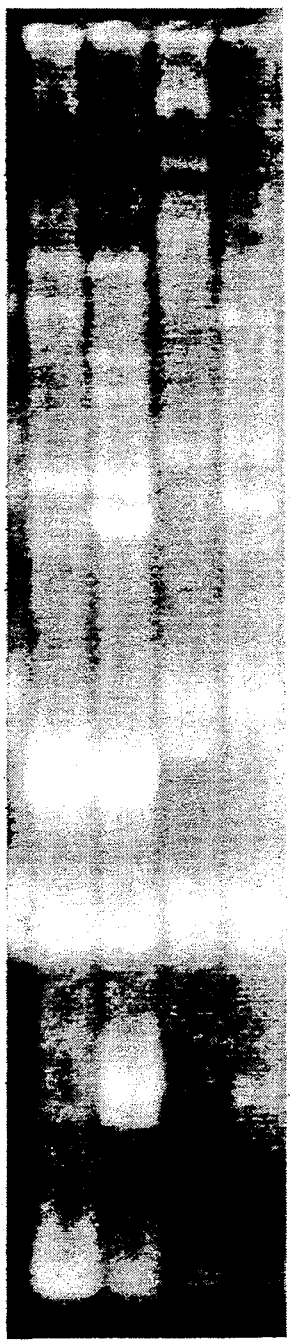
FIG. 1 is an agarose gel electrophoresis of plasmid preparations from B.t. PS81GG and B.t. HD-1.

The novel toxin gene of the subject invention was obtained from a novel lepidopteran-active *B. thuringiensis* (*B.t.*) isolate designated PS81GG.

Characteristics of B.t. PS81GG

Colony morphology--Large colony, dull surface, typical B.t.

Vegetative cell morphology—typical *B.t.*

Flagellar serotype—3a3b, kurstaki.

Intracellular inclusions—sporulating cells produce a bipyramidal crystal which partially encloses a smaller cuboidal crystal.

Plasmid preparations—agarose gel electrophoresis of plasmid preparations distinguishes *B.t.* PS81GG from *B.t.* HD-1 and other *B.t.* isolates.

Alkali-soluble proteins—*B.t.* PS81GG has a 130,000 dalton protein and a 60,000 dalton protein.

Unique toxin—the 130,000 dalton toxin is different from any previously identified.

Activity—*B.t.* PS81 GG kills all Lepidoptera tested, and is twice as active against Beet Armyworm as *B.t.* HD-1.

Beet Armyworm assay results:

*B.t.* PS81GG LC50=4 ug/ml

*B.t.* HD-1 LC50=8 ug/ml

*Spodoptera exigua* Bioassay: Dilutions are prepared of a spore and crystal pellet, mixed with USDA Insect Diet (Technical Bulletin 1528, U.S. Department of Agriculture), and poured into small plastic trays. Neonate *Spodoptera exigua* larvae are placed on the diet mixture and held at 25° C. Mortality is recorded after six days.

*B. thuringiensis* PS81GG, NRRL B-18425, and mutants thereof, can be cultured using standard known media and fermentation techniques. Upon completion of the fermentation cycle, the bacteria can be harvested by first separating the *B.t.* spores and crystals from the fermentation broth by means well known in the art. The covered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. *B.t.* PS81GG, and mutants thereof, can be used to control lepidopteran pests.

A subculture of *B.t.* PS81GG and the *E.* coli host harboring the toxin gene of the invention, *E.* coli NRRL B-18428 was deposited in the permanent collection of the Northern Research Laboratory, U.S. Department of Agriculture, Peoria, Illinois, USA on Oct. 19, 1988. The accession numbers are as follows:

*B.t.* PS81GG NRRL B-18425; deposited Oct. 11, 1988.

*E. coli* (pMYC388)—NRRL B-18428; deposited Oct. 19, 1988.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Acrobacterium, Acetobacter, Lactobacillus, Arthrobacter, Azotobacter, Leuconostoc,* and *Alcaligenes*; fungi, particularly yeast, e.g., genera *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Acrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1QQO bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the Q environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interestgg will be the prokaryotes and the lower eukaryotes, such as fungi. Illustrative prokaryotes, both Gram-negative and -positive, include Enterobacteriaceae, such as Escherichia, Erwinia, Shicella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-stinker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81GG can be made by procedures well known in the art. For example, an asporogenous mutant can be obtained through ethylmethane sulfonate (EMS) mutagenesis of PS81GG. Other mutants can be made using ultraviolet light and nitrosoguanidine by procedures well known in the art.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* PS81GG, NRRL B-18425

A subculture of *B.t.* PS81GG, NRRL B-18425, or mutants thereof, can be used to inoculate the following medium, a peptone, glucose, salts medium.

| | | |
|---|---|---|
| Bacto Peptone | 7.5 | g/l |
| Glucose | 1.0 | g/l |
| KH$_2$PO$_4$ | 3.4 | g/l |
| K$_2$HPO$_4$ | 4.35 | g/l |
| Salt Solution | 5.0 | ml/l |
| CaCl$_2$ Solution | 5.0 | ml/l |
| Salts Solution (100 ml) | | |
| MgSO$_4$.7H$_2$O | 2.46 | g |
| MnSO$_4$.H$_2$O | 0.04 | g |
| ZnSO$_4$.7H$_2$O | 0.28 | g |
| FeSO$_4$.7H$_2$O | 0.40 | g |
| CaCl$_2$ Solution (100 ml) | | |
| CaCl$_2$.2H$_2$O | 3.66 | g |
| pH 7.2 | | |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the

EXAMPLE 2

Cloning of Novel Toxin Gene and Transformation into Escherichia coli

Total Cellular DNA was prepared by growing the cells of *B. thuringiensis* HD-1 and the novel *B.t.* PS81GG to a low optical density ($OD_{600}=1.0$) and recovering the cells by centrifugation. The cells were protoplasted in TES buffer (30 mM Tris-Cl, 10 mM EDTA, 50 mM NaCl, pH 8.0) containing 20% sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was phenol/chloroform (1:1) extracted twice and the DNA precipitated in ethanol. The DNA was purified by isopycnic banding on a cesium chloride gradient.

Total cellular DNA from PS81GG and HD-1 was digested with EcoRI and separated by electrophoresis on a 0.8g Agarose-TAE-buffered gel. A Southern blot of the gel was probed with the NsiI to NsiI fragment of toxin gene contained in the plasmid pM1,130-7 of NRRL B-18332 and the NsiI to KpnI fragment of the "4.5 Kb class" toxin gene (Kronstad and Whitely, [1986]Gene USA 43:29–40). These two fragments were combined and used as the probe. Results show that hybridizing fragments of PS81GG are distinct from those of HD-1. Specifically, a 3.0 Kb hybridizing band in PS81GG was detected instead of the 800 bp larger 3.8 Kb hybridizing band seen in HD-1.

Two hundred migrograms of PSSlOO total cellular DNA was digested with EcoRI and separated by electrophoresis on a preparative 0.8% Agarose-TAE gel. The 2.5 to 3.5 Kb region of the gel was cut out and the DNA from it was electroeluted and concentrated using an ELUTIP™-d (Schleicher and Schuell, Keene, NH) ion exchange column. The isolated EcoRI fragments were ligated to LAMBDA ZAP™ EcoRI arms (Stratagene Cloning Systems, La Jolla, CA) and packaged using GIGAPACK GOLD™ extracts The packaged recombinant phase were plated out with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phase were grown with R4Q8 Mlg helper phase (Stratagene) and the recombinant BLUESCRIPT™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, pM4,31-1, contained an approximate 3.0 Kb EcoRI insert which contained an internal EcoRI site. The cloned fragment was sequenced using Stratagene's T7 and T3 primers plus a set of existing *B.t.* endotoxin oligonucleotide primers.

Total cellular PS81GG DNA was partially digested with AluI or RsaI and digests were mixed. DNA was modified with EcoRI methylase, EcoRI linkers were ligated onto ends, and excess linkers were removed by EcoRI digestion. DNA was size-fractionated on 0.8% Agarose-TAE gels and the approximately 4 to 8 Kb fragments were recovered by electroelution and NACS 52 column chromatography (BRL). Following insert ligation into LAMBDA ZAP™ (Stratagene), which was cut with EcoRI, DNA was packaged into phase heads. Libraries were screened by nucleic acid filter hybridization using a radiolabeled synthetic oligonucleotide probe (CCTGTCGGTTTTTCGGGGCC).

Hybridizing positives were plaque-purified and insert DNA was excised from phase DNA onto pBLUESCRIPT™ plasmid (Stratagene) with helper phase, according to manufacturers directions (Stratagene). The desired plasmid, pMYC388, was restriction mapped and the *B.t.* toxin coding sequence fully characterized by DNA sequencing.

Data from standard insect tests show that the novel *B.t.* PS81GG is active against all Lepidoptera tested.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual.* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, MD, or New England Biolabs, Beverly, MA. The enzymes are used according to the instructions provided by the supplier.

Plasmid pMYC388 containing the *B.t.* toxin gene, can be removed from the transformed host microbe by use of standard well-known procedures. For example, *E. coli* (pMYC388) NRRL B-18428 can be subjected to cleared lysate isopycnic density gradient procedures, and the like, to recover pMYC388.

EXAMPLE 3

Insertion of Toxin Gene Into Plants

The novel gene coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983]Cell 32:1033–1043). A particularly useful vector in this regard is pEND4K (Klee, H. J., Yanofsky, M. F. and Nester, E. W. [1985]Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *B. thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984]Mol. Cell. Biol. 4:399-406), and pAC380, described by Smith et al. (Smith, G. E., Summers, M. D. and Fraser, M. J. [1983]Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel *B.t.* toxin gene is shown in FIG. 2. The deduced amino acid sequence is shown in FIG. 3.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine

X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequence of the *B.t.* toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984]Science 223:249-255). Thus, the subject invention includes mutants of the amino acid sequence depicted herein which do not alter the protein secondary structure, or if the structure is altered, the biological activity is retained to some degree.

We claim:

1. DNA encoding a *B.t.* toxin having the amino acid sequence shown in FIG. 3.

2. DNA, according to claim 1, having the nucleotide sequence shown in FIG. 2.

3. A recombinant DNA transfer vector comprising DNA having the nucleotide sequence which codes for the amino acid sequence shown in FIG. 3.

4. The DNA transfer vector, according to claim 3, transferred to and replicated in a prokaryotic or eukaryotic host.

5. A microorganism which is a bacterial host transformed to express a *B.t.* toxin having the amino acid sequence shown in FIG. 3.

6. A bacterial host according to claim 5, which is *Escherichia coli*, transformed with a plasmid vector containing the *B.t.* toxin gene encoding the *B.t.* toxin having the amino acid sequence shown in FIG. 3.

7. *E. coli* (pMYC388), having the identifying activity against lepidopteran pests characteristics of NRRL B-18428, a host according to claim 5.

8. A microorganism according to claim 5, which is a species of Pseudomonas, Azotobacter, Erwinia, Serratia, Klebsiella, Rhizobium, Rhodopseudomonas, Methylophilius, Agrobacterium, Acetobacter or Alcaligenes.

9. A microorganism according to claim 8, wherein said microorganism is pigmented and phylloplane adherent.

10. Plasmid denoted pMYC388.

* * * * *

UNITED STATES PATENT AND TRADEMARK OFFICE
CERTIFICATE OF CORRECTION

PATENT NO. : 5,135,867
DATED : August 4, 1992
INVENTOR(S) : Jewel Payne, et al

It is certified that error appears in the above-indentified patent and that said Letters Patent is hereby corrected as shown below:

Column 1 line 28: "*Spodoptera exiqua*" should read --*Spodoptera exigua*--.
Column 1 line 45: "500 g to 600 eggs" should read --500 to 600 eggs--.
Column 1 line 68: "and other groups" should read --and other crops--.
Column 2 line 57: "*B.t.* PS81 GG" should read --*B.t.* PS81GG--.
Column 3, lines 6 -7: "The covered *B.t.*" should read --The recovered *B.t.*--.
Column 3 line 66: "can be resulting" should read --can be applied to the environment of target pests(s). The resulting--.
Column 4 line 21: "*Acrobacterium*" should read --*Agrobacterium*--.
Column 4 line 28: "*Acrobacterium*" should read --*Agrobacterium*--.
Column 5 line 48: "1QQQ bp" should read --1000 bp--.
Column 6 line 41: "to the Q environment" should read --to the environment--.
Column 6 line 50: "interestgg will" should read --interest will--.
Column 6 line 53: "*Shicella*" should read --*Shigella*--.
Column 8 line 31: "progedures" should read --procedures--.

UNITED STATES PATENT AND TRADEMARK OFFICE
CERTIFICATE OF CORRECTION

PATENT NO. : 5,135,867
DATED : August 4, 1992
INVENTOR(S) : Jewel Payne, et al

It is certified that error appears in the above-indentified patent and that said Letters Patent is hereby corrected as shown below:

Column 9 line 23: "0.8g Agarose-TAE" should read --0.8% Agarose-TAE--.
Column 9 line 34: "migrograms of PS5100" should read --micrograms of PS81GG--.
Column 9 line 49: "phase were grown with R4Q8 Mlg helper phase" should read --phage were grown with R408 M13 helper phage--.
Column 10 line 4: "phase" should read --phage--.
Column 10 line 11: "phase should read --phage--.

Signed and Sealed this

Fourteenth Day of September, 1993

Attest:

BRUCE LEHMAN

Attesting Officer Commissioner of Patents and Trademarks